United States Patent
Nagao et al.

(10) Patent No.: US 8,854,068 B2
(45) Date of Patent: Oct. 7, 2014

(54) DIAGNOSTIC METHOD FOR OIL-FILLED ELECTRICAL DEVICE, DIAGNOSTIC DEVICE FOR IMPLEMENTING THE DIAGNOSTIC METHOD, AND OIL-FILLED ELECTRICAL DEVICE PROVIDED WITH THE DIAGNOSTIC DEVICE

(75) Inventors: Eiichi Nagao, Chiyoda-ku (JP); Kentaro Taninouchi, Chiyoda-ku (JP); Noboru Hosokawa, Chiyoda-ku (JP); Tsuyoshi Amimoto, Chiyoda-ku (JP); Kozo Tachibana, Chiyoda-ku (JP); Hirotaka Muto, Chiyoda-ku (JP); Junji Tanimura, Chiyoda-ku (JP); Satoru Toyama, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 379 days.

(21) Appl. No.: 12/996,215

(22) PCT Filed: Aug. 18, 2008

(86) PCT No.: PCT/JP2008/064690
§ 371 (c)(1),
(2), (4) Date: Dec. 3, 2010

(87) PCT Pub. No.: WO2010/021017
PCT Pub. Date: Feb. 25, 2010

(65) Prior Publication Data
US 2011/0084716 A1    Apr. 14, 2011

(51) Int. Cl.
| G01R 27/14 | (2006.01) |
| H01F 27/14 | (2006.01) |
| G01N 27/92 | (2006.01) |
| H01F 27/40 | (2006.01) |

(52) U.S. Cl.
CPC .............. *H01F 27/14* (2013.01); *G01R 27/14* (2013.01); *G01N 27/92* (2013.01); *H01F 27/402* (2013.01); *H01F 2027/404* (2013.01)
USPC .......................................... 324/722

(58) Field of Classification Search
CPC ...................................... G01R 27/14
USPC ............................................ 324/722
See application file for complete search history.

(56) References Cited

U.S. PATENT DOCUMENTS

| 5,938,864 A | * | 8/1999 | Tomikawa et al. | 148/435 |
| 6,025,081 A | * | 2/2000 | Ohshiro et al. | 428/644 |

(Continued)

FOREIGN PATENT DOCUMENTS

| JP | 4-176108 A | 6/1992 |
| JP | 5-010911 A | 1/1993 |

(Continued)

OTHER PUBLICATIONS

International Search Report (PCT/ISA/210) issued on Nov. 18, 2008, by Japanese Patent Office as the International Searching Authority for International Application No. PCT/JP2008/064690.

(Continued)

*Primary Examiner* — Jeff Natalini
(74) *Attorney, Agent, or Firm* — Buchanan Ingersoll & Rooney PC

(57) ABSTRACT

An object of the invention is to provide a diagnostic method for an oil-filled electrical device that considers a temperature distribution in the oil-filled electrical device and enables accurate diagnosis to be conducted even when the method is applied to diagnosis of an actually operating device, and further provide a method with which such diagnosis of an oil-filled electrical device can be conducted from a component analysis value of an insulating oil in the oil-filled electrical device. The invention is a diagnostic method for an oil-filled electrical device including in an insulating oil a metal part wrapped with insulating paper, and determines that a time when a surface resistivity of a maximum precipitation site where metal sulfide is most precipitated on the insulating paper reaches a preset surface resistivity management value is a time of occurrence of an abnormality.

11 Claims, 3 Drawing Sheets

(56) References Cited

U.S. PATENT DOCUMENTS

| | | | |
|---|---|---|---|
| 2005/0272959 A1* | 12/2005 | Dyckman et al. | 568/569 |
| 2006/0028216 A1* | 2/2006 | Murase | 324/724 |
| 2007/0049780 A1* | 3/2007 | Schwartz et al. | 585/489 |
| 2010/0192673 A1 | 8/2010 | Toyama et al. | |

FOREIGN PATENT DOCUMENTS

| | | |
|---|---|---|
| JP | 2000-353623 A | 12/2000 |
| JP | 2010-010439 A | 1/2010 |
| JP | 2010-027634 A | 2/2010 |
| WO | 2008/024060 A1 | 2/2008 |

OTHER PUBLICATIONS

Scatiggio et al., "Corrosive Sulfur in Insulating Oils: Its Detection and Correlated Power Apparatus Failures", IEEE Transactions on Power Delivery, Jan. 2008, pp. 508-509, vol. 23, No. 1.

Wiklund et al., "Copper Dissolution and Metal Passivators in Insulating Oil", IEEE Electrical Insulation Magazine, 2007, pp. 6-14, vol. 23, No. 4.

Toyama et al., "High sensitive detection method of dibenzyl disulfide and the elucidation of the mechanism of copper sulfide generation in insulating oil", Doble Client Conference, 2008.

Cigre, "Copper Sulphide in transformer insulation", TF A2.31, ELECTRA, Feb. 2006, pp. 20-23, No. 224.

Qian et al., "Analysis and Treatment of Transformer Fault Caused by Corrosive Sulfur" Transformer, (Jan. 2008), vol. 45, No. 1, pp. 28-30.

Office Action (Grounds for Rejection) dated Sep. 21, 2012, issued in corresponding Chinese Patent Application No. 200880130828.1, and an English Translation thereof. (17 pages).

Bengtsson et al., "Oil Corrosion and Cu2S Deposition in Power Transformers", CIGRE Moscow Symposium 2005, Dec. 31, 2005, pp. 1-5, ABB Power Technologies AB, Ludvika, Sweden XP003018682.

Extended Search Report from European Patent Office on Feb. 7, 2014, issued in corresponding European Patent Application No. 08809025.3.

* cited by examiner

DIAGNOSTIC METHOD FOR OIL-FILLED ELECTRICAL DEVICE, DIAGNOSTIC DEVICE FOR IMPLEMENTING THE DIAGNOSTIC METHOD, AND OIL-FILLED ELECTRICAL DEVICE PROVIDED WITH THE DIAGNOSTIC DEVICE

TECHNICAL FIELD

The present invention relates to an insulation diagnostic method for an oil-filled electrical device such as transformer, for example, made up of parts including a copper part wrapped with insulating paper.

BACKGROUND ART

An oil-filled electrical device such as oil-filled transformer is structured in such a manner that a copper coil, which is a current-carrying medium, is wrapped with insulating paper for preventing the copper coil from being short-circuited between turns adjacent to each other.

It is known that a mineral oil used for the oil-filled transformer contains a sulfur component that reacts with a copper part in the oil to cause electrically-conductive copper sulfide to be precipitated on a surface of the insulating paper, and an electrically-conductive path is formed between turns adjacent to each other, resulting in a problem for example that dielectric breakdown occurs (for example, CIGRE T F A2.31, "Copper sulphide in transformer insulation", ELECTRA, February 2006, No. 224, pp. 20-23 (Non-Patent Document 1)).

Recent studies have revealed that the presence of a specific sulfur compound that is dibenzyl disulfide (hereinafter referred to as DBDS) in an insulating oil causes copper sulfide to be precipitated on a surface of an insulator (for example, F. Scatiggio, V. Tumiatti, R. Marina, M. Tumiatti, M. Pompilli, and R. Bartnikas, "Corrosive Sulfur in Insulating Oils: Its Detection and Correlated Power Apparatus Failures", IEEE Trans. Power Del., January 2008, Vol. 23, pp. 508-509 (Non-Patent Document 2)), and have also revealed a process in which copper sulfide is precipitated from DBDS (for example, S. Toyama, J. Tanimura, N. Yamada, E. Nagao, and T Amimoto, "High sensitive detection method of dibenzyl disulfide and the elucidation of the mechanism of copper sulfide generation in insulating oil", the 2008 Doble Client Conference, Boston, Mass., 2008 (Non-Patent Document 3)).

It is being found that bibenzyl, benzyl sulfide, and toluene that are byproducts generated in the process of precipitation of copper sulfide originating from DBDS can be detected to determine the amount of precipitated copper sulfide from the concentration of the byproducts, since the amount of precipitated copper sulfide is proportional to the byproduct concentration in the insulating oil, and thus an abnormality of the oil-filled electrical device can be diagnosed. Non-Patent Document 3 describes the results of experiments on copper sulfide precipitated on a copper surface of a coil, because the experiments are conducted at a high temperature of 150° C. It is known that, at a temperature of 60° C. to 90° C. which is an operating temperature of the transformer, the copper sulfide precipitated due to dibenzyl disulfide (DBDS) is not precipitated on a copper coil but precipitated on insulating paper.

The inside of the oil-filled electrical device has a temperature distribution. In the case of the transformer, for example, the temperature distribution may include a temperature difference of approximately 20 K. Precipitation of copper sulfide has temperature dependence and precipitation occurs earlier at a higher temperature portion. Because of this, in a device having a temperature distribution, copper sulfide is not uniformly precipitated. The concentration of bibenzyl and toluene for example that is obtained from analysis of components of the insulating oil is proportional to the total amount of copper sulfide precipitated in the whole device. An abnormality of the device occurs at a high temperature portion where precipitation of copper sulfide concentrates, and therefore, diagnosis has to consider the temperature distribution in the device. Thus, there has been a problem that, even if a method in which the concentration of byproducts in the insulating oil is merely measured is applied to diagnosis of an actually operating device, the oil-filled electrical device cannot be diagnosed accurately, because the relationship between an abnormality of the device and detected byproducts is not clear.

It has long been known that copper sulfide is precipitated on a metal surface, which is a different phenomenon from the above-described precipitation of copper sulfide on a surface of insulating paper. In this case, when the amount of generated copper sulfide increases, the copper sulfide could peel off from the metal surface and then float in the insulating oil to deteriorate the insulation performance of the device. As a method for preventing this phenomenon, a method separately provides in the device a detection member with metal particles dispersed on the surface for the purpose of detecting generation of copper sulfide on the metal surface (for example, Japanese Patent Laying-Open No. 04-176108 (Patent Document 1)). This method can detect generation of copper sulfide from a decrease of the surface resistivity of the detection member to diagnose an abnormality of the device.

The diagnostic method disclosed in above-referenced Patent Document 1, however, relates to copper sulfide precipitated on a metal surface as has long been known, and this is a phenomenon different from precipitation of copper sulfide on a surface of insulating paper. Further, the method is accompanied by a problem that the detection member for detecting precipitation of copper sulfide has to be separately provided in the device.

Non-Patent Document 1: CIGRE T F A2.31, "Copper sulphide in transformer insulation", ELECTRA, February 2006, No. 224, pp. 20-23

Non-Patent Document 2: F. Scatiggio, V. Tumiatti, R. Marina, M. Tumiatti, M. Pompilli, and R. Bartnikas, "Corrosive Sulfur in Insulating Oils: Its Detection and Correlated Power Apparatus Failures", IEEE Trans. Power Del., January 2008, Vol. 23, pp. 508-509

Non-Patent Document 3: S. Toyama, J. Tanimura, N. Yamada, E. Nagao, and T. Amimoto, "High sensitive detection method of dibenzyl disulfide and the elucidation of the mechanism of copper sulfide generation in insulating oil", the 2008 Doble Client Conference, Boston, Mass., 2008

Patent Document 1: Japanese Patent Laying-Open No. 04-176108

DISCLOSURE OF THE INVENTION

Problems to be Solved by the Invention

The present invention has been made to solve such problems as described above, and an object of the invention is to provide a diagnostic method for an oil-filled electrical device that considers a temperature distribution in the oil-filled electrical device and enables accurate diagnosis to be conducted even when the method is applied to diagnosis of an actually operating device. It is also an object of the invention to provide a method that enables such diagnosis for an oil-filled electrical device to be conducted from a value obtained from analysis of components of an insulating oil in the oil-filled electrical device.

Means for Solving the Problems

The present invention is a diagnostic method for an oil-filled electrical device including in an insulating oil a metal part wrapped with insulating paper, the diagnostic method determining that a time when a surface resistivity of a maximum precipitation site where metal sulfide is most precipitated on the insulating paper decreases to a preset surface resistivity management value is a time of occurrence of an abnormality.

According to the present invention, preferably the maximum precipitation site is a highest-temperature portion where the temperature is highest on the insulating paper.

Preferably, the surface resistivity management value is a reference value of the surface resistivity that is set so that it can be determined that an abnormality occurs to the device, before dielectric breakdown occurs between coil turns in the oil-filled electrical device, the management value is usually a value larger than a threshold of the surface resistivity at which short circuit occurs between coil turns located at the maximum precipitation site to cause dielectric breakdown, and the management value is set in a range of $1 \times 10^9$ ohm/square to $1 \times 10^{12}$ ohm/square.

For the determination of the time of occurrence of an abnormality according to the present invention, preferably an estimate value of a precipitation amount of metal sulfide at the maximum precipitation site at the time of occurrence of an abnormality is set in advance as a maximum precipitation amount management value ($\rho_0$), and it is determined that a time when the precipitation amount of metal sulfide at the maximum precipitation site reaches the maximum precipitation amount management value is the time of occurrence of an abnormality.

Further, preferably an estimate value of a total precipitation amount of metal sulfide in a whole of the oil-filled electrical device when the precipitation amount of metal sulfide at the maximum precipitation site reaches the maximum precipitation amount management value ($\rho_0$) is set in advance as a total precipitation amount management value ($M_0$), and it is determined that a time when the estimate value ($M_S$) of the total precipitation amount of metal sulfide in the whole of the oil-filled electrical device that is determined from a component analysis value of the insulating oil in the oil-filled electrical device reaches the total precipitation amount management value is the time of occurrence of an abnormality.

Preferably, the component analysis value of the insulating oil is a concentration in the insulating oil of a byproduct generated simultaneously with generation of metal sulfide, and a preferred example of the byproduct is bibenzyl, benzyl sulfide, or toluene.

According to the present invention, preferably the metal part or metal of the metal sulfide is copper.

The present invention is also directed to a diagnostic device for performing the above-described diagnostic method for an oil-filled electrical device, and an oil-filled electrical device provided with the diagnostic device.

Effects of the Invention

The diagnostic method for an oil-filled electrical device of the present invention determines whether an abnormality occurs or not, based on the surface resistivity of a maximum precipitation site where metal sulfide is most precipitated on the insulating paper, and therefore can reliably diagnose whether an abnormality occurs or not even when the amount of precipitated metal sulfide is not uniform throughout the oil-filled electrical device. Particularly, in the case where the surface resistivity of the highest-temperature portion as the above-described maximum precipitation site is used as a reference, the non-uniformity of the amount of precipitated metal sulfide in the device due to the internal temperature distribution of the device and the temperature dependence of copper sulfide precipitation is considered. Therefore, the insulation performance in an actually operating oil-filled electrical device can accurately be diagnosed.

Further, the present invention determines that the time when the estimate value ($M_S$) of the total precipitation amount of metal sulfide in the whole of the oil-filled electrical device, which is determined from a component analysis value of the insulating oil in the oil-filled electrical device, reaches the above-described total precipitation amount management value is the time of occurrence of an abnormality. Thus, without a device for measuring the surface resistivity separately provided in the oil-filled electrical device, the component analysis value of the insulating oil can be used to easily and conveniently detect degradation of the surface resistivity of the insulating paper, and whether or not an abnormality occurs in the oil-filled electrical device can be diagnosed in the simple and convenient manner.

DESCRIPTION OF THE REFERENCE SIGNS 1 copper coil; 2 insulating paper; 3 insulating oil; 4 copper sulfide; 5 electrically conductive path bridging a space between coil turns; 11 coil; 12 washer; 13 oil duct spacer; 14 spacer; 15 flow of insulating oil

BEST MODES FOR CARRYING OUT THE INVENTION

As a manner of a specific diagnostic method of the present invention, a diagnostic method for an oil-filled electrical device includes the steps of:

(i) for a coil used for the oil-filled electrical device, measuring or estimating in advance a threshold of the surface resistivity at which coil turns are short-circuited to cause dielectric breakdown, and setting a certain surface resistivity management value ($R_0$) within a range larger than the threshold of the surface resistivity and smaller than a surface resistivity of insulating paper at which metal sulfide is not precipitated;

(ii) analyzing an internal temperature distribution of the device and determining a highest-temperature portion (heat spot portion) having a highest temperature on the insulating paper in the oil-filled electrical device;

(iii) setting, as a maximum precipitation amount management value ($\rho_0$), an estimate value of the precipitation amount of metal sulfide at the highest-temperature portion when the surface resistivity of the highest-temperature portion decreases to the preset surface resistivity management value ($R_O$) (time of occurrence of an abnormality);

(iv) setting, as a total precipitation amount management value ($M_O$), an estimate value of the total precipitation amount of metal sulfide in the whole of the oil-filled electrical device when the precipitation amount of metal sulfide at the maximum precipitation site reaches the maximum precipitation amount management value ($\rho_O$);

(v) measuring the concentration of a byproduct in an insulating oil and determining an estimate value ($M_S$) of the total precipitation amount of metal sulfide in the whole of the oil-filled electrical device, from the measured concentration; and (vi) diagnosing whether an internal abnormality occurs or not to the oil-filled electrical device, from a relationship in magnitude between the estimate value ($M_S$) of the total precipitation amount of metal sulfide and the total precipitation amount management value ($M_O$).

In the following, a transformer coil (made of copper) is used as an example to describe details of the above-described steps each.

Figure 1:
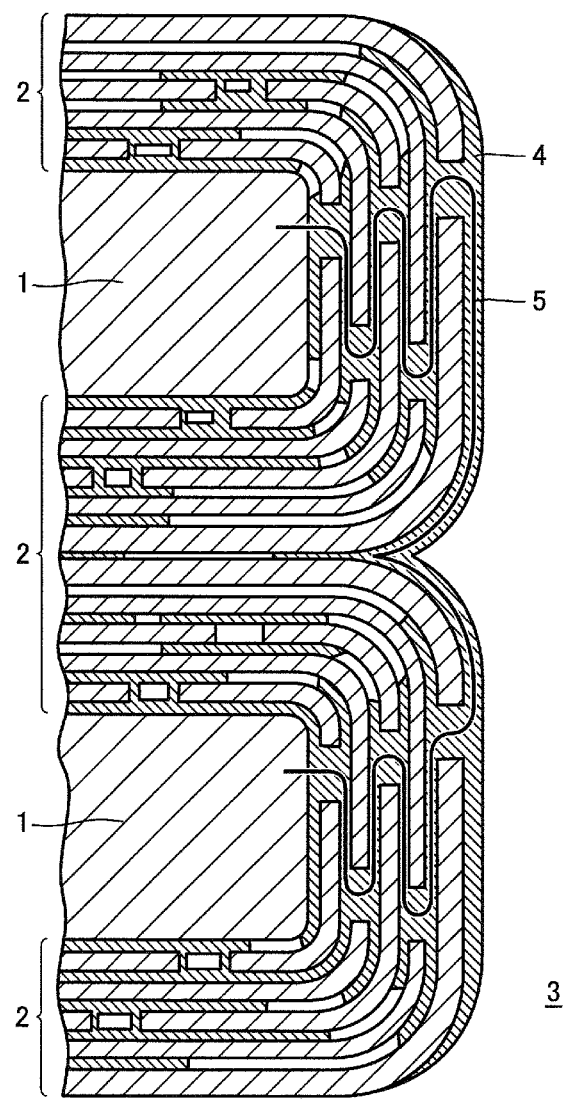
FIG. 1 is a schematic diagram illustrating dielectric breakdown between coil turns due to precipitation of copper sulfide.

First of all, prior to a description of the diagnostic method, a process in which dielectric breakdown occurs to an oil-filled electrical device will be described. FIG. 1 is a schematic diagram illustrating a dielectric breakdown phenomenon between coil turns due to precipitation of copper sulfide. FIG. 1 shows a copper coil 1, insulating paper 2 wrapping this copper coil, an insulating oil 3, copper sulfide 4 precipitated on the insulating paper, and an electrically conductive path 5 formed by the copper sulfide and bridging a space between coil turns. In the insulating oil containing DBDS, copper sulfide 4 is gradually precipitated on a surface of insulating paper 2. When copper sulfide 4 is further precipitated to form electrically conductive path 5 bridging a space between coil turns adjacent to each other, an electric current that normally flows through only the copper coil flows through this electrically conductive path 5 to cause short circuit between the coil turns, resulting in dielectric breakdown.

Figure 2:
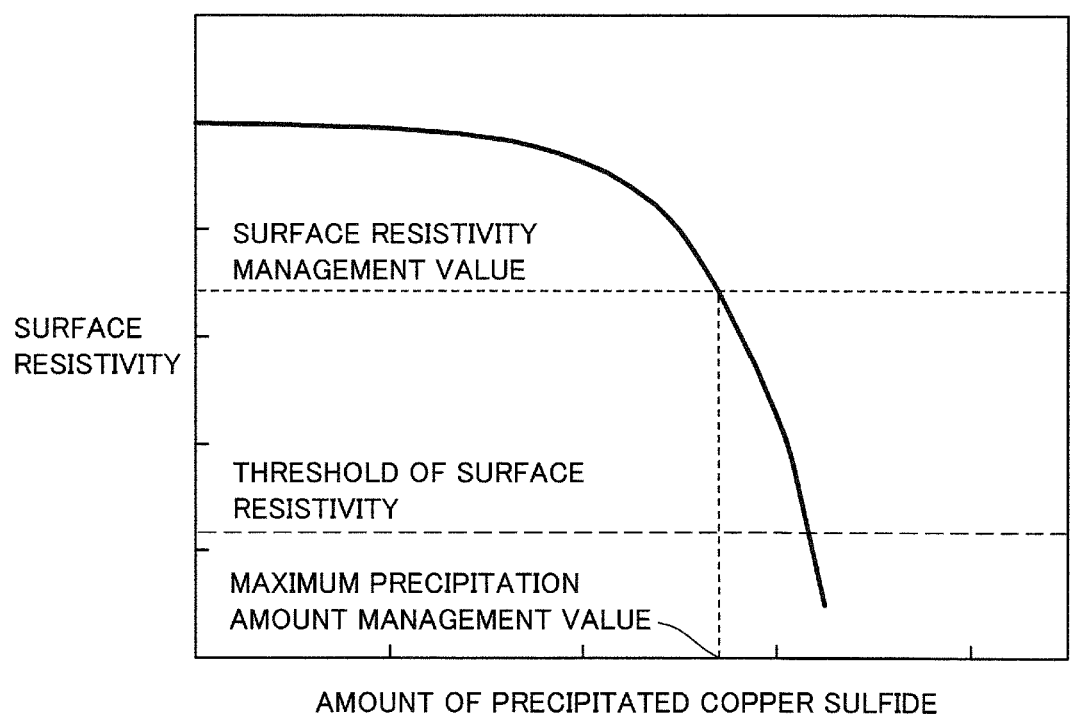
FIG. 2 is a graph illustrating a relationship between an amount of precipitated copper sulfide and a surface resistivity of insulating paper.

Next, the step of setting the surface resistivity management value ($R_O$) (step (i)) will be described. When the electrically conductive path bridging a space between coil turns is formed as described above, the electric current flows via the surface of the insulating paper and, as a pre-phenomenon, the surface resistivity of the insulating paper decreases. FIG. 2 is a graph illustrating a relationship between the amount of precipitated copper sulfide and the surface resistivity of the insulating paper. When the amount of precipitated copper sulfide exceeds a certain value, the surface resistivity of the insulating paper sharply decreases. In FIG. 2, the threshold of the surface resistivity is a threshold of the surface resistivity at or below which short circuit occurs between coil turns to cause dielectric breakdown. The surface resistivity management value which is set in the present invention is a reference value of the surface resistivity that is set so that whether or not an abnormality occurs to the device can be determined before dielectric breakdown between coil turns occurs, and is usually a value larger than the above-described threshold of the surface resistivity.

The insulating paper before copper sulfide is precipitated thereon has a surface resistivity of $1 \times 10^{14}$ ohm/square or more. When dielectric breakdown between coil turns occurs due to copper sulfide, the insulating paper has a surface resistivity of $1 \times 10^7$ ohm/square to $1 \times 10^9$ ohm/square. Therefore, the above-described surface resistivity management value is set to a certain value preferably in a range of $1 \times 10^9$ ohm/square to $1 \times 10^{12}$ ohm/square and more preferably in a range of $1 \times 10^{10}$ ohm/square to $1 \times 10^{11}$ ohm/square.

Figure 3:
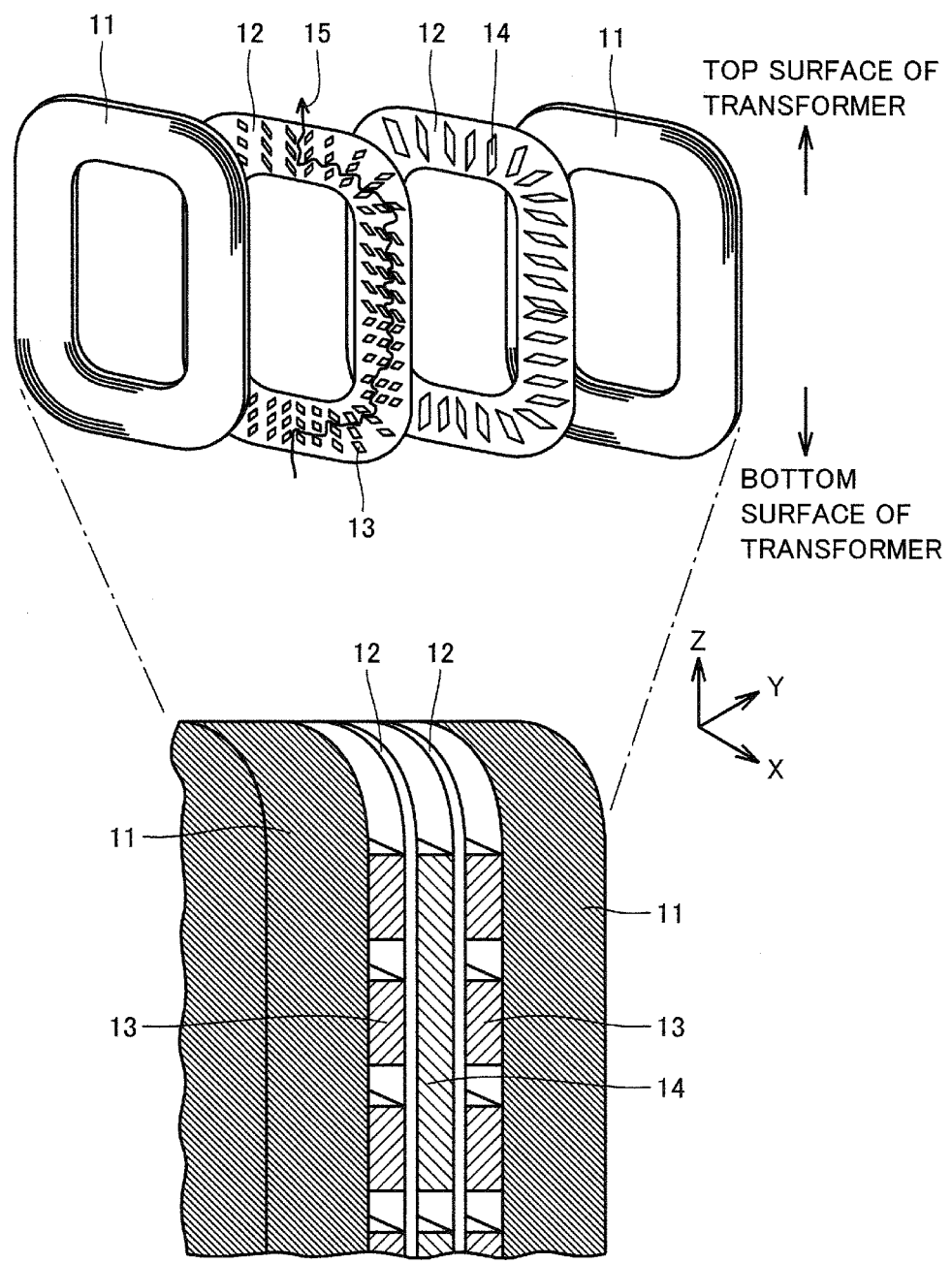
FIG. 3 is a schematic diagram illustrating a coil structure of a shell-type transformer.

Next, a description will be given of the step of analyzing an internal temperature distribution of the device and determining a highest-temperature portion (heat spot portion) where the temperature is highest on the insulating paper in the oil-filled electrical device (step (ii)). First, the internal temperature distribution of the oil-filled electrical device will be described using FIG. 3 (schematic diagram showing a coil structure of a shell-type transformer). FIG. 3 shows a coil 11, a washer 12 insulating adjacent coils from each other, an oil duct spacer 13 arranged for providing an oil flow space on the coil-side surface of the washer, a spacer 14 provided between washers, and an insulating oil flow 15. Here, 12 to 14 are formed by a pressboard and made of cellulose that is the same material as that for the insulating paper. Copper sulfide is precipitated not only on a surface of the coil's insulating paper but also on the pressboard (on washer 12, oil duct spacer 13 and spacer 14) of the same material, namely cellulose.

The insulating oil also serves as a cooling medium for the coil. As the insulating oil flows between coils as indicated by 15, the oil temperature increases. Thus, the oil temperature at the top surface of the transformer is higher than the oil temperature at the bottom surface thereof. Accordingly, the temperature of the insulating paper and the pressboard (washer 12, oil duct spacer 13, and spacer 14) on which copper sulfide is precipitated is also higher at a site closer to the top surface of the transformer. Further, the direction in which the insulating oil flows, the flow path and the flow rate of the insulating oil for example also influence the temperature distribution in the transformer. Furthermore, while FIG. 1 shows a coil of two layers, a coil of more than ten layers is arranged in an actual transformer, and the arrangement of the coil also influences the temperature distribution in the transformer. In general, a coil arranged at a central portion has a higher temperature than the coils arranged on the opposite ends in the transformer. Therefore, temperature T of the insulating paper and the pressboard on which copper sulfide is precipitated varies in a three-dimensional manner and is represented by a variable (T (x, y, z)) for a three-dimensional position represented by means of the x, y, and z axes shown in FIG. 3.

For the oil-filled electrical device having such a temperature distribution, the internal temperature distribution of the device is analyzed from a specification for the oil-filled electrical device or from the result of a heat run test. From the result of the analysis, a portion of the highest temperature (highest-temperature portion) in the oil-filled electrical device is determined.

Here, it is known that the precipitation amount of copper sulfide has temperature dependence and the precipitation rate is approximately doubled as the temperature increases by 10 K. As described above, since the temperature distribution in the transformer is not uniform, the precipitation amount of copper sulfide is not uniform in the transformer. The precipitation amount of copper sulfide on the insulating paper wrapping the copper coil or on the pressboard is also represented by a variable $\rho$ (x, y, z) that varies in a three-dimensional manner correspondingly to T (x, y, z). At a portion of a higher temperature in the oil-filled electrical device, precipitation of copper sulfide occurs earlier. Therefore, the highest-temperature portion where T (x, y, z) is maximum corresponds to a maximum precipitation site where $\rho$ (x, y, z) is maximum (where metal sulfide is most precipitated).

The step of setting the maximum precipitation amount management value ($\rho_O$) (step (iii)) will be described. First, by means of a model experiment or the like, an estimate value is determined in advance of the precipitation amount of copper sulfide at the highest-temperature portion (maximum precipitation site) when the surface resistivity of the insulating paper at the highest-temperature portion reaches the surface resistivity management value. The estimate value is set as the maximum precipitation amount management value ($\rho_0$). Here, $\rho_0$ is a reference value used for determining that an abnormality occurs (the surface resistivity of the insulating paper at the maximum precipitation site exceeds the above-described surface resistivity management value), based on the fact that copper sulfide of an amount exceeding $\rho_0$ is precipitated on the insulating paper.

Next, the step of setting the total precipitation amount management value ($M_0$) (step (iv)) will be described. Here, based on the result of the analysis of the internal temperature distribution of the oil-filled electrical device conducted in above-described step (ii), an estimate value of the total precipitation amount of copper sulfide in the whole of the device when the precipitation amount of copper sulfide ($\rho$) at the highest-temperature portion reaches the maximum precipitation amount management value ($\rho_0$) is calculated, and the calculated estimate value is set as the maximum precipitation amount management value ($M_0$). Namely, it is supposed that the precipitation amount of metal sulfide is completely proportional to the temperature, and then the precipitation amount of metal sulfide at each site is determined based on the maximum precipitation amount management value ($\rho_0$) and the result of the analysis of the internal temperature distribution, and the sum of respective amounts of respective sites is determined for use as the total precipitation amount management value ($M_0$).

The total precipitation amount ($M_0$) of the copper sulfide in the whole of the oil-filled electrical device is the sum of respective amounts ($\rho(x, y, z)$) of copper sulfide precipitated at respective sites in the transformer, and is represented by the following expression (1).

$$M(t) = \iiint \rho(z, y, z) \quad (1)$$

The above-described precipitation amount management value ($\rho_0$) is the maximum value of $\rho(x, y, z)$. Copper sulfide in the oil-filled electrical device is precipitated not only on the insulating paper wrapping the copper coil but also on the pressboard (washer 12, oil duct spacer 13, and spacer 14 in FIG. 3). The insulating paper wrapping the copper coil which is a heat source is higher in temperature than the pressboard. Therefore, the precipitation amount ($\rho(x, y, z)$) of copper sulfide at the highest-temperature portion on the insulating paper is $\rho_0$.

Next, a description will be given of the step of measuring the concentration of a byproduct in the insulating oil and determining an estimate value ($M_S$) of the total precipitation amount of metal sulfide in the whole of the oil-filled electrical device, from the measured concentration (step (v)). The total precipitation amount of copper sulfide in the oil-filled electrical device is proportional to the amount of generated byproduct (such as bibenzyl) that is generated as the copper sulfide is generated in the insulating oil. Thus, the estimate value ($M_S$) of the total precipitation amount of metal sulfide in the whole of the oil-filled electrical device as determined from a component analysis value of the insulating oil in the oil-filled electrical device can be determined from the following expression:

$$M_S = K \cdot C \cdot W_0$$

where K is a proportionality constant, C is the concentration of a byproduct in the insulating oil, and $W_0$ is the total weight of the insulating oil. Namely, proportionality constant K may be determined in advance through a model experiment, calculation or the like to determine an estimate value ($M_S$) of the total precipitation amount of metal sulfide in the whole of the oil-filled electrical device, as determined from a component analysis value of the insulating oil in the oil-filled electrical device.

It should be noted that another byproduct such as benzyl sulfide and toluene may be used as the above-described byproduct, instead of bibenzyl, to determine the value of $M_S$ in a similar manner to the above-described manner.

Finally, the step of diagnosing whether or not an internal abnormality occurs to the oil-filled electrical device (step (vi)) will be described. From the relationship in magnitude between the total precipitation amount management value ($M_0$) determined in the above-described manner and the estimate value ($M_S$) of the total precipitation amount of metal sulfide in the whole of the oil-filled electrical device as determined from a component analysis value of the insulating oil in the oil-filled electrical device, the following diagnostic result is obtained:

the device is normal when $M_S < M_0$, and
the device is abnormal when $M_S \geq M_0$.

It should be construed that embodiments disclosed herein are by way of illustration in all respects, not by way of limitation. It is intended that the scope of the present invention is defined by claims, not by the above description of the embodiments, and includes all modifications and variations equivalent in meaning and scope to the claims.

The invention claimed is:

1. A method for diagnosing an oil-filled electrical device including a transformer and a metal part wrapped with insulating paper in insulating oil, said diagnostic method comprising:
   a) storing a preset surface resistivity management value;
   b) receiving a surface resistivity measurement value from a sensor, wherein the sensor is placed at a maximum precipitation site where metal sulfide is most precipitated on the insulating paper;
   c) comparing the surface resistivity measurement value to the preset resistivity management value;
   d) determining that the oil-filled electrical device is in an abnormal condition when the surface resistivity value is less than or equal to the preset surface resistivity management value; and determining that the oil-filled electrical device is in a normal condition when the surface resistivity value is greater than the preset surface resistivity management value,
   wherein steps b, c and d are performed while the oil-filled electrical device is operating.

2. The according to claim 1, wherein said maximum precipitation site is a highest-temperature portion on the insulating paper.

3. The method according to claim 1, wherein said surface resistivity management value is a value larger than a threshold of the surface resistivity at which short circuit occurs between coil turns located at said maximum precipitation site to cause dielectric breakdown.

4. The method according to claim 1, wherein said surface resistivity management value is a value in a range of $1 \times 10^9$ ohm/square to $1 \times 10^{12}$ ohm/square.

5. The method according to claim 1, wherein an estimate value of a precipitation amount of metal sulfide at said maximum precipitation site is set in advance as a maximum precipitation amount management value, and it is determined that the oil-filled device is in an abnormal condition when the precipitation amount of metal sulfide at said maximum precipitation site reaches said maximum precipitation amount management value.

6. The method according to claim 5, wherein an estimate value of a total precipitation amount of metal sulfide in a whole of the oil-filled electrical device when the precipitation amount of metal sulfide at said maximum precipitation site reaches said maximum precipitation amount management value is set in advance as a total precipitation amount management value, and it is determined that a time when the estimate value of the total precipitation amount of metal sulfide in the whole of the oil-filled electrical device that is determined from a component analysis value of the insulating oil in the oil-filled electrical device reaches the total precipitation amount management value is a time when the precipitation amount of metal sulfide at said maximum precipitation site reaches said maximum precipitation amount management value.

7. The method according to claim 6, wherein said component analysis value of the insulating oil is a concentration in the insulating oil of a byproduct generated simultaneously with generation of metal sulfide.

8. The method according to claim 7, wherein said byproduct is bibenzyl, benzyl sulfide, or toluene.

9. The method according to claim 1, wherein said metal is copper.

10. A diagnostic device that diagnoses an oil-filled electrical device including a transformer and a metal part wrapped with insulating paper in insulating oil, configured to:
   a) store a preset surface resistivity management value;
   b) receive a surface resistivity measurement value from a sensor, wherein the sensor is placed at a maximum precipitation site where metal sulfide is most precipitated on the insulating paper;
   c) compare the surface resistivity measurement value to the preset resistivity management value;
   d) determine that the oil-filled electrical device is in an abnormal condition when the surface resistivity value is less than or equal to the preset surface resistivity management value; and determine that the oil-filled electrical device is in a normal condition when the surface resistivity value is greater than the preset surface resistivity management value,
   wherein the diagnostic device performs steps b, c, and d while the oil-filled electrical device is operating.

11. A device comprising:
an oil-filled electrical device including a transformer and a metal part wrapped with insulating paper in insulating oil; and
a diagnostic device configured to:
   a) store a preset surface resistivity management value;
   b) receive a surface resistivity measurement value from a sensor, wherein the sensor is placed at a maximum precipitation site where metal sulfide is most precipitated on the insulating paper;
   c) compare the surface resistivity measurement value to the preset resistivity management value;
   d) determine that the oil-filled electrical device is in an abnormal condition when the surface resistivity value is less than or equal to the preset surface resistivity management value; and determine that the oil-filled electrical device is in a normal condition when the surface resistivity value is greater than the preset surface resistivity management value,
   wherein the diagnostic device performs steps b, c, and d while the oil-filled electrical device is operating.

* * * * *